United States Patent [19]

Reiner

[11] Patent Number: 4,784,992

[45] Date of Patent: Nov. 15, 1988

[54] PHOSPHORYLALKANOLAMIDE DERIVATIVES OF L-CARNITINE AND PHARMACEUTICAL COMPOSITIONS CONTAINING SAME

[75] Inventor: Alberto Reiner, Como, Italy

[73] Assignee: Sigma-Tau Industrie Farmaceutiche Riunite S.p.A., Italy

[21] Appl. No.: 397

[22] Filed: Jan. 5, 1987

[30] Foreign Application Priority Data

Jan. 13, 1986 [IT] Italy .................................. 47524 A/86

[51] Int. Cl.$^4$ ........................ A61K 31/685; C07F 9/10
[52] U.S. Cl. ........................................ 514/77; 558/170
[58] Field of Search ................... 558/174, 170; 514/76, 514/77

[56] References Cited

U.S. PATENT DOCUMENTS 4,218,404 8/1980 Feuer et al. ..................... 558/170

Primary Examiner—Anton H. Sutto
Attorney, Agent, or Firm—Ladas & Parry

[57] ABSTRACT

Amide derivatives of L-carnitine of formula

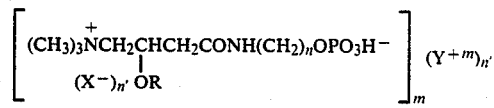

wherein:
R is H or a straight or branched alkanoyl group having 2–6 carbon atoms;
$X^-$ is the anion of a pharmacologically acceptable acid;
$Y^{+m}$ is the cation of an alkaline or alkaline-earth metal;
n is an integer from 1 to 6;
n' is either 0 or 1; and
m is either 1 or 2, are more active than L-carnitine in restoring to normal in the myocardium the metabolism of fatty acids imbalanced by the administration of erucic acid. Pharmaceutical compositions containing such derivatives are effective for therapeutical treatment of hyperlipidemias, atherosclerosis and cardiovascular and metabolic disturbances related thereto.

8 Claims, No Drawings

PHOSPHORYLALKANOLAMIDE DERIVATIVES OF L-CARNITINE AND PHARMACEUTICAL COMPOSITIONS CONTAINING SAME

The present invention relates to L-carnitine phosphorylalkanolamides of general formula

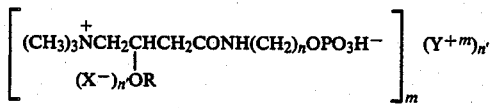

wherein:
R is H or a straight or branched alkanoyl group having 2-6 carbon atoms;
$X^-$ is the anion of a pharmacologically acceptable acid;
$Y^{+m}$ is the cation of an alkaline or alkaline-earth metal;
n is an integer from 1 to 6;
n' is either 0 or 1; and
m is either 1 or 2.

Preferably, the alkanoyl group is selected among acetyl, propionyl, butyryl or isobutyryl; $X^-$ is $Cl^-$. It should be understood that, if in formula (I) n'=0, the amide derivatives present themselves as inner salts of formula (I bis):

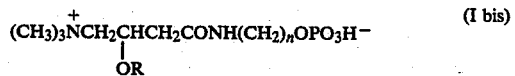

If, on the other hand, in formula (I) n'=1, the amide derivatives present themselves as either alkaline metal salts (m=1) or alkaline-earth metalsalts (m=2).

The present invention also relates to orally or parenterally administrable pharmaceutical compositions for the therapeutical treatment of hyperlipidemias, atherosclerosis and the cardiovascular disturbances related thereto, coronary sclerosis and myocardium sclerosis and generally of all myocardial and cerebral ischaemic conditions, for profilaxis and therapy of the myocardial and cerebral infarction and biliary calculosis, which comprises a therapeutically effective amount of one of the above-identified amide derivatives and a pharmacologically acceptable excipient.

Carnitine has long been known to be effective in restoring to normal any imbalance in lipid metabolism. In fact, U.S. Pat. No. 4,255,449 discloses the use of carnitine for treating abnormal levels in haematic lipoproteins, particularly for increasing the plasma level in high density lipoproteins (HDL) so as to selectively reduce the ratio of low density (LDL) and very low density lipoproteins (VLDL) to high density lipoproteins (HDL) in patients in which that ratio is abnormally above the normal range of about 1.5 to 2.7. U.S. Pat. No. 4,315,944 further discloses the use of carnitine in the treatment of hyperlipidemias, i.e the increase of the overall amount of lipids in blood regardless of their nature: overall cholesterol, tryglicerides, phospholipids and free fatty acids.

It has now been found that the phosphorylalkanolamides of L-carnitine according to the present invention are remarkably more potent than carnitine in restoring to normal any imbalance in the lipid metabolism.

The process for preparing the compounds of the present invention wherein R is H, $X^-$ is $Cl^-$, n is 2 and $Y^{+m}$ is $Ca^{+2}$, essentially comprises:

(1) chlorinating acetyl L-carnitine chloride with a chlorinating agent selected among thionyl chloride, phosphorus oxychloride and phosphorus pentachloride, at about 5° C.–40° C., for about 10-20 hours in an organic solvent selected among dichlomethane, chloroform and tetrahydrofurane until a clear solution of the acid chloride of acetyl L-carnitine chloride is obtained;

(2) reacting the solution of the acid chloride of acetyl L-carnitine chloride with an alkaline solution of beta-aminoethanolphosphoric acid at about 0° C.–5° C. for about 2-8 hours, keeping the resulting reaction mixture under stirring for about 9-10 hours; concentrating the mixture under vacuum after adjusting its pH to 3-4 and taking up the residue with an organic solvent, thus bringing about the precipitation of inorganic salts and unreacted compounds which are filtered off; rconcentrating the filtrate and dissolving the concentrate in water, then passing the resulting solution through ion exchange resins for removing the sodium and chloride ions; concentrating the resulting solution, taking it up with methanol and reacting it with a concentrated solution of calcium chloride, thus obtaining the calcium salt of L-carnitine phosphorylethanolamide; and (3) converting the calcium salt of L-carnitine phosphorylethanolamide into the corresponding inner salt by passing an aqueous solution of calcium salt through a suitable ion exchange resin.

The L-carnitine phosphorylalkanolamides wherein R is alkanoyl are prepared via a similar process, starting from the corresponding alkanoyl L-carnitine chloride, taking care to carry out the chlorination reaction according to procedures well known to the experts in these synthesis under sufficiently mild conditions as not to bring about the hydrolysis of the O-alkanoyl groups and using in step (2) the appropriate aminoalkanolphosphoric acid.

The preparation of compounds according to the present invention is illustrated in the following, non-limiting examples.

EXAMPLE 1

Preparation of L-carnitine phosphorylethanolamide (1) Preparation of the acid chloride of acetyl L-carnitine chloride.

Acetyl L-carnitine chloride (110 grams; 0.458 moles) was suspended in dichloromethane. To the resulting suspension (450 ml) which was kept under stirring, thionyl chloride (36.6 ml; 0.504 moles) was added directly. The reaction mixture was kept under stirring until a clear solution was obtained. The reaction was completed after 18 hours. Upon termination of the chlorination, the reaction mixture was concentrated under vacuum to half of its initial volume, the concentrate was taken up with dichloromethane and the resulting solution was concentrated under vacuum to give a rather fluidd oil. This oil was used as such in the subsequent reaction.

(2) Preparation of the calcium salt of L-carnitine chloride phosphorylethanolamide.

2.55 moles of NaOH (scales) were dissolved in 550 ml of water. To the resulting solution, 72.13 grams (0.511 moles) of beta-aminoethanolphosphoric acid were added at a temperature of about 5° C. Under stirring and keeping the temperature between 0° C. and 5° C. a solution of 110 grams (0.426 moles) of the acid chloride of acetyl L-carnitine chloride dissolved in 110 ml of dichloromethane was slowly added. The dichloromethane solution was poured uniformly over about 3 hours. The temperature was allowed to raise to room temperature while keeping the reaction mixture under stirring. The pH was adjusted to 3.5-4 with concentrated hydrochloric acid while keeping the mixture under stirring till the reaction was completed. The resulting reaction mixture was then concentrated under vacuum at a top temperature of 45° C. to give an oily mass rich in salts. The concentrate was taken up with 800 ml of methanol and, after the mixture was allowed to stand for 4 hours, the remaining precipitate, which was shown to consist of inorganic salts and unreacted product, was filtered off. The concentrated alcoholic solution yielded an oil which was dissolved in water and passed through a strongly acidic ion exchange resin (AMBERLITE IR 120) activated with a diluted aqueous solution of hydrochloric acid and subsequently through a weakly basic resin (AMBERLITE IR 45 already in activated form). The aqueous solution thus obtained was concentrated under vacuum, taken up with 400 ml of methanol and, after it had been heated up to 40° C., treated with a concentrated aqueous solution (1:1 by weight) of 16 grams of calcium chloride. The calcium salt of L-carnitine phosphorylethanolamide precipitated. The salt was filtered, washed with alcohol and then with acetone. The salt, freed from possible carnitine impurities exhibited a typical HPLC chromatogram consisting of a single peak.

(3) Preparation of the inner salt of L-carnitine phosphorylethanolamide.

A 20% aqueous solution of the calcium salt of L-carnitine phosphorylethanolamide was passed through AMBERLITE IR 120 activated with a 10% solution of hydrochloric acid. The eluate was neutralized with AMBERLITE IR 45 resin. The solution was then concentrated to dryness under vacuum. A white product crystallized which was taken up with warm ethanol. The inner salt of L-carnitine phosphorylethanolamide precipitated and showed the following chemico-physical characteristics: White, amorphous, hygroscopic powder. Soluble in water and methanol at room temperature and in warm ethanol; insoluble in most of the common organic solvents.

Chromatographical behaviour (a) TLC

A 10% water solution (5 μl) was placed on a aluminium plate coated with silica gel (Merck-Bracco n. 5554) and eluted with a 7CH$_3$OH/3CHCl$_3$/1NH$_4$OH (v/v/v) mixture. The plate dried in an air stream and exposed to iodine vapours showed a spot corresponding to the title product. R$_f$=0.1

(b) HPLC

An aqueous solution of the inner salt of L-carnitine phosphorylethanolamide (concentration: 5 mg/ml) was injected into a LC Varian 5020 chromatograph at the following conditions:

| Column | Supelcosil - NH$_2$, 25 × 4.6 mm, 5μ |
|---|---|
| Eluent: | A CH$_3$CN |
| | B 0.05 M KH$_2$PO$_4$ |
| | 25% B for 15 minutes; subsequently, to 35% over a 3-minute period. |
| Flow rate: | 1.3 ml/min. for 15 minutes; subsequently 2 ml/min. till analysis end. |

| Reading: | 205 nm |
|---|---|
| Loop: | 10 μl |
| Retention time: | 23.7 minutes |

The peak of the compound under examination is distinctly separate from both the carnitine peak and the acetyl carnitine peak as well as from the peaks of the other intermediates for synthesizing carnitine, which are eluted before 23 minutes have elapsed.

(c) Specific Optical rotation

An aqueous solution of the compound under examination (concentration: 0.9 grams/100 ml) was placed in the 5-ml cell (optical path=10 cm) of a Perkin Elmer 243 polarimeter. $[\alpha]_D^{20} = -8.09$.

(d) U.V. spectrophotometry

An aqueous solution of the compound under examination (concentration: 20 μg/ml) showed maximum absorption at 190 nm. The absorbtion markedly decreased as the wave length increased and at 210 nm it practically overlapped the bottom line.

(e) I.R. spectophotometry

The I.R. spectrum was performed in KBr using a Perkin Elmer 1310 spectophotometer. The absorption bands which distinguish the present compound from carnitine are as follows absorption bands present in the L-carnitine phosphorylethanolamide spectrum and absent in the carnitine spectrum, which bands are attributable to the amide carbonyl:

1660 cm$^{-1}$ strong 1560 cm$^{-1}$ medium absorption bands absent in the L-carnitine phosphorylethanolamide spectrum and present in the carnitine spectrum, which bands are attributable to the carboxilic carbonyl:

1600 cm$^{-1}$ strong 1700 cm$^{-1}$ weak (f) Elementary analysis

The elemntary analysis of C$_9$H$_{21}$O$_6$N$_2$PH$_2$O gave the following results:

| | Found | Calculated |
|---|---|---|
| C | 35.67% | 35.76% |
| H | 7.71% | 7.67% |
| N | 9.26% | 9.27% |

(g) NMR spectrometry

The NMR-$^1$H spectra showed the characteristic signals of the carnitine methyl, methylene and

radicals and the two methylene radicals of the aminoethanolphosphate group.

PHARMACOLOGICAL TRIALS

A myocardial steatosis model, in which an L-carnitine positive effect was already described, was used in the rat. The steatosis was induced by adding, for five (5) consecutive days, erucic acid-rich rape oil in the rats' normal daily diet, according to the method described by Branca et al. (Internat., Vit. Nutr. Res., 47, 162-166, 1977). Trial-groups of six (6) male Wistar rats, weighing from 190 g to 220 g, were used.

The results obtained are shown in Table 1.

L-carnitine phosphorylethanolamide, endoperitoneally-administered at the dose of 250 mg/Kg for five (5) days reduced the accumulation of triglycerides in the myocardium, lowered the cholesterol levels and brought back to normal the ATP values. These effects were statistically significant with Student's t test.

Table 2 shows the results obtained with L-carnitine treatment (250 mg/kg endoperitoneally for 5 days) using the same test-model, namely the myocardial steatosis induced by the administration of erucic acid-rich rape oil.

TABLE 1

Effects of L-carnitine phosphoryletanolamide on the erucic acid-induced myocardial steatosis.

| Treatment | n° animals | Triglycerides mg/g of fresh tissue | Cholesterol mg/g of fresh tissue | ATP nM/g proteines |
|---|---|---|---|---|
| Controls | 6 | 3401 ±552.3 | 32.7 ±11.95 | 34.2 ±8.73 |
| L-carnitine phosphoryl-ethanolamide 250 mg/kg e.p. | 6 | 1773 ±454.4 −47.9% P < 0.001 | 12.8 ±7.16 −60.9% P < 0.01 | 60.5 ±5.78 +76.9% P < 0.001 |

TABLE 2

Effects of L-carnitine on theerucic acid-induced myocardial steatosis in the rat

| Treatment | n° animals | Triglycerides mg/g of fresh tissue | Cholesterol mg/g of fresh tissue | ATP nM/g proteines |
|---|---|---|---|---|
| Controls | 6 | 3401 ±552.3 | 32.7 ±11.95 | 34.2 ±8.73 |
| L-carnitine 250 mg/g e.p. | 6 | 1357 ±423.6 −60.1% P < 0.001 | 24.7 ±7.01 −34.5% n.s. | 57.3 ±20.28 ±67.5% P < 0.05 |

The effects of L-carnitine phosphorylethanolamide to Irwin's test in the mouse and acute toxicity after endoperitoneal administration of the substance, always in the mouse, were also evaluated.

The relative results are shown in Tables 3 and 4.

TABLE 3

Effects of L-carnitine phosphorylethanolamide on the normal mouse's behaviour

| Doses mg/kg e.p. | Number of animals | Main effects observed |
|---|---|---|
| 1000 | 4 M + 4 F | apparently normal |
| 2000 | 4 M + 4 F | Slight muscular hypotonia and palpebral ptosis; phenylkynone-type muscle strains. |
| 4000 | 4 M + 4 F | Slight muscular hypotonia and palpebral ptosis. |
| 8000 | 4 M + 4 F | Sedation; muscular hypotonia and palpebral ptosis; intermittent tremors. |

TABLE 4

Mortality curve and L-carnitine phosphorylethanolamide's $LD_{50}$ in the mouse

| Doses mg/kg e.p. | Number of animals | N° of dead animals* | $LD_{50}$ |
|---|---|---|---|
| 1000 | 4 M + 4 F | 0 | >8000 mg/kg e.p. |
| 2000 | 4 M + 4 F | 0 | |
| 4000 | 4 M + 4 F | 0 | |
| 8000 | 4 M + 4 F | 0 | |

TABLE 4-continued

Mortality curve and L-carnitine phosphorylethanolamide's $LD_{50}$ in the mouse

*7 days observation.

The model of erucic acid-induced myocardial steatosis is used to compare the effect of the 14 day-administration of 250 and 125 mg/kg e.p. of L-carnitine with that of L-carnitine phosphorylethanolamide at the same doses for the same study period.

L-carnitine (free, total, esterified, etc.) plasmatic and tissue levels and the creatinphosphate levels in the heart were also evaluated in this trial, together with the already examined parameters.

Moreover other tests were carried out using a model of olive-oil induced hyperlipemia in the rat. L-carnitine was administered at 250 and 125 mg/kg endoperitoneally for 14 days, as was L-carnitine phosphorylethanolamide at 250 and 125 mg/kg endoperitoneally for 14 days. The following parameters were evaluated:

In the serum: Kilomicrons, beta-lipoproteines, lipoproteines, alpha-lipoproteines, triglycerides, phospholipids, cholesterol, and carnitine.

In the myocardium: Triglycerides, cholesterol, ATP, creatinphosphate, acetyl-CoA and carnitine.

Summarizing, the results of the various pharmacological trials carried out indicate that L-carnitine phosphorylethanolamide is extremely active in the normalization of myocardial hypertriglyceridemia and hyperlipemia, induced by erucic acid treatment. Moreover it is efficacious in re-establishing the balance between fatty acids' oxidation and uptake, and in stimulating acetyl-CoA's oxidation in Kreb's cycle. Important to underline is that to these actions, another, of a more ubiquitary nature, must be added. This activity can be considered as being "free fatty acids scavenger", thanks to which the free hydroxyl is capable of exporting certain fatty acids from the cell, in particular those fatty acids which cannot be used by the cell itself and that must thus be removed, such as lactic acid.

The L-carnitine phosphoryletanolamide's capacity of promoting muscular and, in general, tissular lactic acid wash-out, practically translates itself in an action which is vitally important for the ischemic cell.

It is in fact known that during processes of tissular anoxya, the cellular's oxygen balance is negative; in these conditions the aerobic glycosis cannot take place, whereas the anaerobic glycosis continues, producing however, only small quantities of ATP, barely sufficient for the cell's survival in conditions of reduced performance. If however the condition of anoxya lasts too long, the accumulation of lactic acid gives way to a decrease of the intracellular pH, which causes the inhibition of various enzymatic systems.

The consequences for the cell are fatal, since they become ischemic and die. This gives way to the formation of ischemic zones in the cerebral and cardiac precincts and subsequent myocardial infarction, cerebral ischemia etc. Thus the use of a drug capable of buffering the intracellular pH exporting the lactic acid from the cell, garantees, even in a state of anoxya, the maintenance of the anaerobic glycolitic processes and thus the cell's survival.

The L-carnitine phosphorylethanolamide's activity of ubiquitary nature, "free fatty acid scavenger" amplifies the substance's therapeutic nature comprising the various forms of dislipemia. It is known that the fatty acids do not undergo renal clearance, since they are metabolised through the beta-oxidation meccanism. If the fatty acids are transported by L-carnitine phosphorylethanolamide, it is possible to solubilize them and therefore do not interact with the plasmatic proteines, originating glomerular filtration meaning they are not reabsorbedd in the tubulus renalis: pratically there is a renal clearance of the fatty acids which has the effect of normalizing the lipidic metabolism. The consequence of this meccanism is evident: the decrease of fatty acids determines a decrease of the various lipidic fractions, including cholesterol.

The net polarity of the molecule of L-carnitine phosphorylethanolamide stimulates moreover the desaturation process of cholesterol in the bile, avoiding the formation of calcules and facilitating their dissolution.

L-carnitine phosphorylethanolamide is therefore useful in indications such as anoxya, ischemia at any tissular level or intracellular fraction, caused by contingent conditions or having a chronic course, with particular reference to the profilaxis.

At the same time, L-carnitine phosphorylethanolamide is indicated in the various forms of dislipemia, in alterations of the lipidic metabolism, in forms of hypercholesteroemia, in the prevention and the therapy of biliar calcolosis. According to the same above mentioned rationale, L-carnitine phosphorylethanolamide is active in the forced wash-out of drugs having acidic characteristics, such as anti-inflammatory non-steroideal agents.

The daily dose to be administered will be determined having regard to the age, weight and general conditions of the patient. Effective results can be obtained with doses as low as 5-10 mg/kg of body weight/day. However, in view of the extremely low toxicity of the L-carnitine amide derivatives of the present invention, larger doses can be safely administered, such as 15-20 mg/kg of body weight/day.

The compounds of the present invention are compounded into the usual pharmaceutical compositions which comprise solid and liquid, orally or parenterally administrable unit dosage forms.

Non limiting examples of orally and, respectively, parenterally administrable composition in unit dosage form, are as follows:

(a) injectable compostion:

| | | |
|---|---|---|
| L-carnitine phosphorylethanolamide | mg | 100 |

| | | |
|---|---|---|
| -continued | | |
| water for injections, balance to | ml | 2 |

(b) compostions for tablets

| | | |
|---|---|---|
| L-carnitine phosphorylethanolamide | mg | 400 |
| stearic acid | mg | 50 |
| microcrystalline cellulose | mg | 35 |
| L-carnitine phosphorylethanolamide | mg | 500 |
| starch | mg | 200 |
| microcrystalline cellulose | mg | 100 |
| talc | mg | 50 |

What is claimed is:

1. A method for treating myocardial steatosis which comprises administering to a patient an effective amount of a composition comprising an inner salt of L-carnitine of the formula

2. A method, as in claim 1 wherein the effective amount comprises 15-20 mg/kg of body weight per day.

3. A method, as in claim 1 wherein the effective amount comprises 5-10 mg/day.

4. An inner salt of L-carnitine phosphorylethanolamide of the formula:

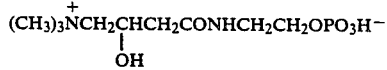

5. A pharmaceutical composition for the therapeutical treatment of myocardial steatosis which comprises a therapeutically effective amount of L-carnitine phosphorylalkanolamide of the formula

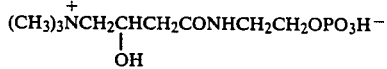

and a pharmaceutically acceptable excipient.

6. The pharmaceutical composition, as in claim 5 wherein the effective amount comprises from about 200 to about 500 mg of the carnitine phosphorylalkanolamide.

7. A composition, as in claim 6 wherein the composition is in the form of a liquid or solid.

8. A composition, as in claim 7 wherein the composition is in the form of a tablet.

* * * * *